(12) United States Patent
Van Lankvelt et al.

(10) Patent No.: US 9,134,201 B2
(45) Date of Patent: Sep. 15, 2015

(54) FLUID PROVIDING APPARATUS

(75) Inventors: Petrus Johannes Wilhelmus Van Lankvelt, Boekel (NL); Dominique Maria Bruls, Eindhoven (NL); Albert Hendrik Jan Immink, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 1273 days.

(21) Appl. No.: 13/000,031

(22) PCT Filed: Jun. 22, 2009

(86) PCT No.: PCT/IB2009/052661
§ 371 (c)(1),
(2), (4) Date: Dec. 20, 2010

(87) PCT Pub. No.: WO2010/001295
PCT Pub. Date: Jan. 7, 2010

(65) Prior Publication Data
US 2011/0093213 A1    Apr. 21, 2011

(30) Foreign Application Priority Data
Jul. 2, 2008  (EP) .................................. 08104600

(51) Int. Cl.
*G01N 35/10*  (2006.01)
*G01N 1/02*  (2006.01)
*G01N 35/00*  (2006.01)

(52) U.S. Cl.
CPC ............ *G01N 1/02* (2013.01); *G01N 35/00584* (2013.01); *G01N 35/10* (2013.01); *G01N 2001/028* (2013.01)

(58) Field of Classification Search
CPC ............ A61M 5/142; A61M 5/14212; A61M 5/14276; G01N 21/55; G01N 21/59
USPC ............................................................ 702/23
See application file for complete search history.

(56) References Cited

U.S. PATENT DOCUMENTS 5,192,506 A * 3/1993 Kureshy et al. ................. 422/64
5,736,403 A   4/1998 Riall
(Continued)

FOREIGN PATENT DOCUMENTS

EP    1389445 A2    2/2004
GB    2339615 A     2/2000

OTHER PUBLICATIONS

Kolbrich, Erin A. et al "Cozart RapiScan Oral Fluid Drug Testing System: An Evaluation of Sensitivity, Specificity, and Efficiency for Cocaine Detection Compared with ELISA and GC-MS Following Controlled Cocaine Administration" Journal of Analytical Toxicology, vol. 27, Oct. 2003, pp. 407-411.

*Primary Examiner* — Janet Suglo
*Assistant Examiner* — Michael Dalbo

(57) ABSTRACT

The invention relates to a fluid providing apparatus (5; 34) for providing a fluid to an analyzing apparatus (17; 33) for analyzing the fluid and to the analyzing apparatus (17; 33). The fluid providing apparatus (34) comprises a casing (35), which has an introduction opening (7), through which a fluid transferring element (1) is introducible into the casing (35) for transferring the fluid to the fluid providing apparatus (34). The casing (35) comprises further a fluid releasing section (8) for releasing the fluid from the fluid transferring element (1) and a fluid transferring element detection section (36) for detecting whether the fluid transferring element (1) is introduced into the casing (35) by interacting with a fluid transferring element detection unit of the analyzing apparatus (17; 33).

4 Claims, 10 Drawing Sheets

(56) References Cited

U.S. PATENT DOCUMENTS

| | | | |
|---|---|---|---|
| 5,925,021 A * | 7/1999 | Castellano et al. | 604/207 |
| 6,377,894 B1 * | 4/2002 | Deweese et al. | 702/22 |
| 2002/0143272 A1 * | 10/2002 | Crawford et al. | 600/573 |
| 2004/0082878 A1 * | 4/2004 | Baldwin et al. | 600/573 |
| 2004/0189311 A1 * | 9/2004 | Glezer et al. | 324/444 |
| 2005/0227370 A1 * | 10/2005 | Ramel et al. | 436/514 |
| 2007/0031914 A1 * | 2/2007 | Zhu et al. | 435/25 |
| 2007/0154922 A1 | 7/2007 | Collier | |
| 2007/0172388 A1 * | 7/2007 | Padmanabhan et al. | 422/58 |
| 2007/0208274 A1 | 9/2007 | Ostrowski | |
| 2007/0239069 A1 | 10/2007 | Guirguis | |
| 2008/0118397 A1 | 5/2008 | Slowey | |
| 2009/0011451 A1 * | 1/2009 | Rodriguez et al. | 435/29 |
| 2009/0035746 A1 * | 2/2009 | Ehben et al. | 435/4 |

\* cited by examiner

FLUID PROVIDING APPARATUS

FIELD OF THE INVENTION

The invention relates to a fluid providing apparatus for providing a fluid to an analyzing apparatus for analyzing the fluid. The invention further relates to an analyzing apparatus, an analyzing method and a computer program for analyzing a fluid provided by the fluid providing apparatus, and to an analyzing system for analyzing a fluid comprising the fluid providing apparatus and the fluid analyzing apparatus.

BACKGROUND OF THE INVENTION

A system for analyzing a fluid is, for example, a system for analyzing saliva comprising a disposable cartridge and a reading apparatus. A disposable swab-stick is provided for collecting a saliva sample and for transferring the same to the disposable cartridge for providing the saliva sample to the reading apparatus for analyzing the provided saliva sample. Generally, a sealed package is provided comprising the disposable swab-stick and the disposable cartridge. In a standard procedure the cartridge is inserted into the reading apparatus and then the swab-stick is used to collect a saliva sample. When the saliva sample has been collected, it can be mixed with a buffer fluid. Subsequently, the buffered sample can be applied to the cartridge and the buffered saliva flows through a filtering section and reagent releasing section into an analyzing section, in which the saliva is analyzed by using the reader. This system for analyzing a fluid is disclosed in the article "Cozart® RapiScan Oral Fluid Drug Testing System: An Evaluation of Sensitivity, Specificity, and Efficiency for Cocaine Detection Compared with EIA and GC-MS Following Controlled Cocaine Administration", Erin A. Kolbrich et al., Journal of Analytical Toxicology, Vol. 27, October 2003.

When the cartridge is inserted into the reading apparatus, the reading apparatus detects the presence of the cartridge and the detection electronics for analyzing the saliva sample are switched on. In the period between cartridge detection and fluid assaying or analyzing the sample needs to be collected. This collecting of the sample takes at least 30 seconds in the average and might take up to some minutes. Moreover, time is needed for handling by the operator. During this period the detection electronics are switched on. This consumes unnecessary power in the reading apparatus.

SUMMARY OF THE INVENTION

It is an object of the present invention to provide a fluid providing apparatus for providing a fluid to an analyzing apparatus for analyzing the fluid and an analyzing apparatus, an analyzing method and a computer program for analyzing a fluid provided by the fluid providing apparatus, and an analyzing system for analyzing a fluid comprising the fluid providing apparatus and the fluid analyzing apparatus, wherein the power consumption of the analyzing apparatus can be reduced.

In an aspect of the present invention a fluid providing apparatus for providing a fluid to an analyzing apparatus for analyzing the fluid is disclosed, the fluid providing apparatus comprising a casing having:
  an introduction opening, through which a fluid transferring element is introducible into the casing for transferring the fluid to the fluid providing apparatus,
  a fluid releasing section for releasing the fluid from the fluid transferring element,
  a fluid transferring element detection section for detecting whether the fluid transferring element is introduced into the casing by interacting with a fluid transferring element detection unit of the analyzing apparatus,
  a control unit for switching on or off the analyzing apparatus depending on the detection of the fluid transferring element within the fluid providing apparatus.

The invention is based on the idea that generally the reader device of an analyzing unit does not have to be in an operating state, until the fluid transferring element has been introduced into the fluid providing apparatus. The fluid transferring element detection section allows detecting whether the fluid transferring element is introduced into the casing by interacting with a fluid transferring element detection unit of the analyzing apparatus and, therefore, to operate, in particular, switch on or off, the reader device of the analyzing apparatus depending on the detection of the fluid transferring element within the fluid providing apparatus. This reduces unnecessary power consumption of the reader device of the analyzing apparatus.

The fluid providing apparatus allows an analyzing apparatus to switch, for example, an analyzing unit for analyzing the fluid from a non-analyzing mode to an analyzing mode, in particular, to switch the analyzing unit on, only if a fluid transferring element detection unit of the fluid analyzing apparatus has detected whether the fluid transferring element is introduced into the casing by interacting with the fluid transferring element detection section. Thus, if, for example, the fluid providing apparatus, which might be a cartridge, has been introduced into the fluid analyzing apparatus, which can be regarded as a reading apparatus, the analyzing unit, which can comprise detection electronics for analyzing the fluid, could be switched on, only if it has been detected that the fluid transferring element, which can be a swab-stick, has been inserted into the fluid providing apparatus. The time, during which the analyzing unit of the analyzing apparatus is switched on, can therefore be reduced, which allows to reduce the power consumption of the analyzing apparatus.

It is preferred that the fluid transferring element detection section comprises at least one optical transparent portion for allowing to optically detect whether the fluid transferring element is introduced into the casing. This allows detecting whether the fluid transferring element has been introduced into the casing in a contactless way, without the presence of mechanical wear. Furthermore, an optical detection generally does not require additional parts of the fluid providing apparatus or sub-assemblies. It is only required that the fluid providing apparatus comprises at least one optical transparent portion. This keeps the costs of the fluid providing apparatus low.

It is further preferred that the at least one optical transparent portion is adapted to allow fluid transferring element detection light of a light source of the fluid transferring element detection unit of the analyzing apparatus to enter the fluid transferring element detection section for optically detecting whether the fluid transferring element is introduced into the casing. It is further preferred that the at least one optical transparent portion is adapted to allow the fluid transferring element detection light to transmit through the fluid transferring element section. This allows to determine whether the fluid transferring element has been introduced into the casing by determining whether the fluid transferring element detection light, which has entered the fluid transferring element detection section through the at least one optical transparent portion, is at least partly blocked by the fluid transferring element. The at least one optical transparent portion can also be adapted such that it can be determined whether the fluid transferring element has been introduced into the casing by detecting whether the fluid transferring element detection light is reflected by the fluid transferring element within the fluid transferring element detection section. The optical transparent portion is preferentially a portion of the casing at the transferring element detection section being transparent to the fluid transferring element detection light. Furthermore, this at least one optical portion is preferentially adapted such that the fluid transferring element detection light can enter and leave the fluid transferring element detection section of the casing as required by the corresponding fluid transferring element detection unit of the fluid analyzing apparatus.

It is further preferred that the fluid providing apparatus comprises an analyzing section for analyzing the fluid released from the fluid transferring element by interacting with an analyzing unit of the analyzing apparatus.

The fluid providing apparatus is preferentially a cartridge, which is preferentially disposable. The fluid providing apparatus is preferentially adapted to provide a liquid like, for example, saliva, urine or blood or another liquid. The fluid providing apparatus can also be adapted to provide a gas.

The fluid transferring element comprises preferentially a swab and is preferentially a swab-stick. Also the fluid transferring element is preferentially disposable and is adapted for being introducible into the fluid providing apparatus. The preferred swab of the fluid transferring element is preferentially adapted to collect a sample of a fluid like a liquid, for example, saliva, urine, or blood.

The fluid transferring element detection section and the fluid releasing section are preferentially located at the same place or close to each other within the fluid providing apparatus and are preferentially integrated. The fluid transferring element detection section is preferentially a part of the fluid releasing section. This allows detecting whether the fluid transferring element has been introduced into the fluid releasing section by the fluid transferring element detection section. Since preferentially the analyzing unit of the fluid analyzing apparatus has to be switched from a non-analyzing mode to an analyzing mode, in particular, has to be switched on, only, if fluid has been released from the fluid transferring element, i.e. if the fluid transferring element has been introduced into the fluid releasing section, and since firstly the fluid transferring element is introduced through the introduction opening into the casing and enters the fluid releasing section later, this further reduces the power consumption of the analyzing apparatus, without affecting the analysis or the assay adversely.

It is further preferred that the casing comprises a fluid detection section for detecting whether the fluid has entered the analyzing section by interacting with a fluid detection unit of the analyzing apparatus. This allows detecting whether a fluid, which has been released in the fluid releasing section, has entered the analyzing section. Therefore, if, for example, a flow of the fluid from the fluid releasing section to the analyzing section is disturbed, this can be detected by the fluid detection section and the fluid detection unit of the analyzing apparatus, and, in this case, the analyzing apparatus can be switched from an analyzing mode to a non-analyzing mode, in particular, switched off and/or an alert signal can be output to a user.

The fluid detection section and the analyzing section are preferentially located at the same place or close to each other or are integrated into each other within the casing of the fluid providing apparatus. Preferentially the fluid detection section is a part of the analyzing section and is preferentially located at the beginning of the analyzing section with respect to a flow direction of the fluid.

In a further preferred embodiment, the fluid providing apparatus comprises at least two fluid detection sections located at the beginning and the end of the analyzing section with respect to the flow direction of the fluid. This allows determining whether the fluid has traversed the analyzing section. Preferentially, this allows monitoring if the analyzing section is filled completely. So firstly it is seen at the beginning of the analyzing section that the fluid has entered the analyzing section, in particular, that wetting has occurred at the beginning of the analyzing section. Then, generally, it can be seen that the fluid has reached the end of the analyzing section, in particular, that wetting has occurred at the end of the analyzing section. In this case, preferentially, it can be determined that the sensing area is completely 'wetted' i.e. covered with fluid. Also, by monitoring the time required between the determination at the beginning of the analyzing section and at the end of the analyzing section, in particular, by monitoring the time required to fill the analyzing section completely, information about the fluid can be gained about, for example, the viscosity of the fluid, by measuring the time required for the fluid to move from a first fluid detection section to a second fluid detection section, in particular, to move from a first wetting sensor to second wetting sensor.

Preferentially, the fluid detection section comprises an optical transparent portion for allowing to optically detect whether the fluid has entered the analyzing section. This allows to detect whether the fluid has entered the analyzing section in a contactless way and without the presence of mechanical wear. In addition, it is generally not necessary to have additional parts or sub-assemblies of the fluid providing apparatus, which keeps the manufacturing costs of the fluid providing apparatus low.

Also this optical transparent portion is adapted such that light can enter the casing, in particular, the fluid detection section of the casing. Furthermore, this optical transparent portion of the fluid detection section is adapted such that light can be used for optically detecting whether the fluid has entered the analyzing section as required by the fluid detection unit of the fluid analyzing apparatus.

In a preferred embodiment, the fluid releasing section is adapted to squeeze the fluid transferring element for releasing the fluid. It is further preferred that the fluid releasing section has a decreasing diameter in a direction away from the introduction opening, i.e. which points from the fluid releasing section to the location of the analyzing section. This allows to release the fluid from the fluid transferring element by the same operation, which is used for introducing the fluid transferring element into the casing.

It is further preferred that the casing comprises a filtering section comprising a filter for filtering the fluid released from the fluid transferring element. This allows filtering parts of the fluid out of the fluid, which could disturb the analysis, in particular, the measurement, or the assay in the analyzing section, thereby improving the analysis or the assay. A further filter can also be present to remove bubbles from the fluid, in particular, from saliva.

The invention also discloses an analyzing apparatus for analyzing a fluid provided by a fluid providing apparatus comprising a casing having an introduction opening, through which a fluid transferring element is introducible into the casing for transferring the fluid to the fluid providing apparatus, as defined in claim 1, the analyzing apparatus comprising:

a fluid transferring element detection unit for detecting whether the fluid transferring element is introduced into the casing by interacting with a fluid transferring element detection section of the fluid providing apparatus, a control unit for switching on or off the analyzing apparatus depending on the detection of the fluid transferring element within the fluid providing apparatus.

In a preferred embodiment, the fluid transferring element detection unit comprises:
- a light source for generating fluid transferring element detection light for entering the fluid transferring element detection section of the fluid providing apparatus through an optical transparent portion of the fluid transferring element detection section,
- a reflected light detector for detecting reflected light reflected by the fluid transferring element for optically detecting whether the fluid transferring element is introduced into the casing of the fluid providing apparatus. This allows to determine whether the fluid transferring element has been introduced into the casing by determining whether the reflected light has been modified by introducing the fluid transferring element into the casing, in particular, by determining whether the intensity of the reflected light has been increased or decreased in order to detect whether light is reflected by the fluid transferring element or not.

It is further preferred that the fluid transferring element detection unit comprises:
- a light source for generating fluid transferring element detection light for entering the fluid transferring element detection section of the fluid providing apparatus through at least one optical transparent portion of the fluid transferring element detection section,
- a transmitted light detector for detecting transmitted light transmitted through the fluid transferring element detection section through the at least one optical transparent portion for optically detecting whether the fluid transferring element is introduced into the casing of the fluid providing apparatus. This allows detecting whether the fluid transferring element has been introduced into the casing by determining whether the transmitted light has been modified by introducing the fluid transferring element into the casing, in particular, by determining whether the intensity of the transmitted light has been increased or decreased, for example, by determining whether light is transmitted through the transferring element detection section or whether light is not transmitted through the fluid transferring element detection section, i.e. whether light is blocked by the fluid transferring element within the fluid transferring element detection section.

In a preferred embodiment, the analyzing apparatus further comprises an analyzing unit for analyzing fluid released from the fluid transferring element by a fluid releasing section of the fluid providing apparatus by interacting with an analyzing section of the fluid providing apparatus, wherein the analyzing unit comprises an analyzing mode and a non-analyzing mode.

It is further preferred that the analyzing apparatus comprises a control unit for controlling the fluid transferring element detection unit and the analyzing unit such that the analyzing unit is switched from the non-analyzing mode to the analyzing mode, if the fluid transferring element detection unit determines that the fluid transferring element has been introduced into the casing of the fluid providing apparatus.

Since the control unit is adapted such that the analyzing unit is switched from the non-analyzing mode to the analyzing mode, if the fluid transferring element detection unit determines that the fluid transferring element has been introduced into the casing of the fluid providing apparatus, the analyzing unit is only operated in the analyzing mode, if the fluid transferring element has indeed been introduced into the casing of the fluid providing apparatus, i.e. if a fluid is expected to enter the analyzing section of the fluid providing apparatus for analyzing the fluid by the analyzing unit. This reduces the power consumption of the analyzing unit and, thus, of the analyzing apparatus.

In the non-analyzing mode the analyzing unit is preferentially switched off and in the analyzing mode the analyzing unit is preferentially switched on.

In a preferred embodiment, the analyzing apparatus comprises a fluid detection unit for detecting whether the fluid has entered the analyzing section of the fluid providing apparatus by interacting with a fluid detection section of the fluid providing apparatus. This allows to detect whether the fluid has entered the analyzing section of the fluid providing apparatus, wherein, for example, the analyzing unit can be switched into the non-analyzing mode, in particular, can be switched off, if the fluid detection unit detects that fluid has not entered the analyzing section after a predetermined time after detecting the fluid transferring element in the fluid transferring element detection section, thereby further reducing the power consumption. In this case, alternatively or in addition an alert signal can be output.

In a preferred embodiment, the fluid providing apparatus comprises at least two fluid detection units located at the beginning and the end of the analyzing section with respect to the flow direction of the fluid, if the fluid providing apparatus has been inserted into the analyzing apparatus. This allows determining whether the fluid has traversed the analyzing section.

It is further preferred that the fluid detection unit comprises a light source for generating fluid detection light and a fluid detection light detector for optically detecting whether the fluid has entered the analyzing section of the fluid providing apparatus. This allows to optically detect whether the fluid has entered the analyzing section or not, thereby providing a contactless method, which can be robust and free of mechanical wear. Furthermore, preferentially the optical detection method does not require additional parts or sub-assemblies of the fluid providing apparatus, which keeps the costs of the fluid providing apparatus low.

In a preferred embodiment, the analyzing apparatus comprises a determination unit for determining whether after a predetermined time interval after a detection of the fluid transferring element by the fluid transferring element detection unit the fluid has not been detected by the fluid detection unit. Preferentially, the analyzing apparatus comprises an output unit for outputting a signal, if the determination unit determines that after a predetermined time interval after detection of the fluid transferring element by the fluid transferring element detection unit the fluid has not been detected by the fluid detection unit. It is further preferred that the control unit is adapted to switch the analyzing unit to the non-analyzing mode, if the determination unit determines that after a predetermined time interval after a detection of the fluid transferring element by the fluid transferring element detection unit the fluid has not been detected by the fluid detection unit.

In a further embodiment, the fluid detection section of the fluid providing apparatus and the fluid detection unit of the analyzing apparatus are located at a location downstream of the fluid releasing section with respect to the flow of the fluid, wherein this location does not have to be within the analyzing section. This allows determining failures in the fluid flow in the fluid providing apparatus, in particular, in the cartridge.

In a further aspect of the present invention an analyzing system for analyzing a fluid comprising the fluid providing apparatus as defined in claim 1 and the fluid analyzing apparatus as defined in claim 6 is presented.

In a further aspect of the present invention an analyzing method for analyzing a fluid provided by a fluid providing apparatus comprising a casing for receiving a fluid transferring element as defined in claim 1 is presented, wherein the analyzing method comprises the step of detecting whether the fluid transferring element is introduced into the casing by interacting with a fluid transferring element detection section of the fluid providing apparatus by a fluid transferring element detection unit.

Preferentially, the analyzing method further comprises the step of analyzing fluid released from the fluid transferring element by a fluid releasing section of the fluid providing apparatus by interacting with an analyzing section of the fluid providing apparatus by an analyzing unit, wherein the analyzing unit comprises an analyzing mode and a non-analyzing mode.

It is further preferred that the analyzing method comprises the step of controlling the fluid transferring element detection unit and the analyzing unit such that the analyzing unit is switched from the non-analyzing mode to the analyzing mode, if the fluid transferring element detection unit determines that the fluid transferring element has been introduced into the casing of the fluid providing apparatus, by a control unit.

In a further aspect of the present invention a computer program for analyzing a fluid provided by a fluid providing apparatus comprising a casing for receiving a fluid transferring element is presented, wherein the computer program comprises program code means for causing an analyzing apparatus as defined in claim 6 to carry out the steps of the analyzing method as defined in claim 13, when the computer program is run on a computer controlling the analyzing apparatus.

It shall be understood that the fluid providing apparatus of claim 1, the analyzing apparatus of claim 6, the analyzing system of claim 13, the analyzing method of claim 14 and the computer program of claim 15 have similar and/or identical preferred embodiments as defined in the dependent claims. Disclosed are examples of the invention in which the control unit is comprised in the fluid providing apparatus and alternatively comprised in the analyzing apparatus.

It shall be understood that a preferred embodiment of the invention can also be any combination of the dependent claims with the respective independent claim.

BRIEF DESCRIPTION OF THE DRAWINGS

These and other aspects of the invention will be apparent from and elucidated with reference to the embodiments described hereinafter. In the following drawings.

DETAILED DESCRIPTION OF EMBODIMENTS

Figure 1:
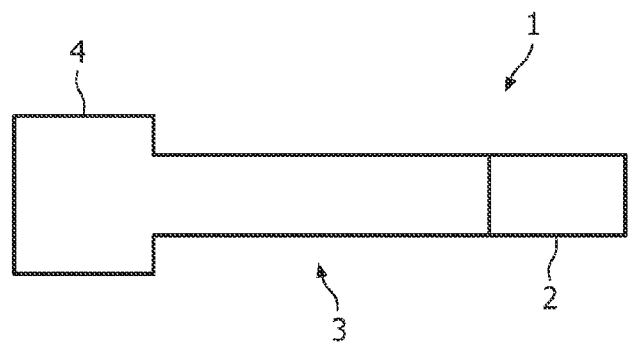
FIG. 1 shows schematically and exemplarily an embodiment of a fluid transferring element.

FIG. 1 shows schematically and exemplarily an embodiment of a fluid transferring element, which is, in this embodiment, a swab-stick 1. The swab-stick 1 comprises a swab 2 for receiving a sample of a fluid like a liquid, for example, a sample of saliva or blood. The swab-stick 1 further comprises a stick 3, which comprises a first end portion, to which the swab 2 is attached, and a second end portion, which comprises a grip 4.

The fluid transferring element 1, i.e., in this embodiment, the swab-stick 1, is introducible into a casing 35 of a fluid providing apparatus 34 through an introduction opening 7. A sectional view through the fluid providing apparatus 34 is schematically and exemplarily shown in FIG. 2. The fluid providing apparatus 34 is, preferentially, a cartridge, which is preferentially disposable. Also the fluid transferring element 1 is preferentially disposable.

The fluid providing apparatus 34 comprises the casing 35 including the introduction opening 7, through which the fluid transferring element 1 is introducible into the casing 35 for transferring the fluid to the fluid providing apparatus 34. The casing 6 further comprises a fluid releasing section 8 for releasing the fluid from the fluid transferring element 1, i.e., in this embodiment, from the swab 2 of the swab-stick 1. The fluid releasing section 8 is adapted to squeeze the fluid transferring element 1, i.e., in this embodiment, the swab 2 of the swab-stick 1, for releasing the fluid. The releasing section has a decreasing diameter in a direction away from the introduction opening 7 such that the swab 2 of the swab-stick 1 is squeezed if introduced and pressed into the casing 35, in particular, into the fluid releasing section 8.

The fluid providing apparatus 34 further comprises a fluid transferring element detection section 36 for detecting whether the fluid transferring element 1 is introduced into the casing 35 by interacting with a fluid transferring element detection unit of an analyzing apparatus 33, which will be described further below. The fluid transferring element detection section 36 is located at the same place, at which the fluid releasing section 8 is located, in order to determine whether the fluid transferring element has been introduced into the fluid releasing section, in particular, in this embodiment, in order to determine whether the swab 2 of the swab-stick 1 has been introduced into the fluid releasing section 8.

The fluid transferring element detection section 36 comprises at least one optical transparent portion 10, 23 for allowing to optically detect whether the fluid transferring element 1 has been introduced into the casing 35. In this embodiment, the at least one optical transparent portion 10, 23 is adapted such that fluid transferring element detection light of a light source of a fluid transferring element detection unit of an analyzing apparatus 33, which will be described further below, can enter the fluid transferring element detection section and leave the fluid transferring element detection section at the location, which is opposite to the location, at which the fluid transferring element detection light has entered the fluid transferring element detection section, in order to allow the fluid transferring element detection light to transmit through the fluid transferring element detection section, if the fluid transferring element 1, in particular, the swab 2 of the swab-stick 1, has not been introduced into the casing 35, in particular, into the fluid releasing section 8. This allows to optically detect whether the fluid transferring element 1 has been introduced into the casing 35 of the fluid providing apparatus 34 by determining whether the fluid transferring element 1 blocks the fluid transferring element detection light or at least a part of the fluid transferring element detection light within the fluid transferring element detection section.

The casing 35 further comprises a filtering section 14 including a filter 15 for filtering the fluid released from the fluid transferring element 1, in particular, released from the swab 2 of the swab-stick 1. The filter element is preferentially a SaF filter, through which the fluid, in particular, saliva or blood, is squeezed. The filter 15 can also be adapted to remove bubbles from the fluid, in particular, from saliva or blood. Preferentially buffer components are added by drying them in a SaF and debubbling filter. When the fluid, in particular, saliva or blood, flows through the SaF and de-bubbling filter, the buffer components are redispersed.

In particular, during drying a filter is drenched in a buffer solution, which is, in this embodiment, needed for the assay. After the buffer has 'dried up' the buffer components, such as salts and proteins, remain in the filter. If now the fluid is introduced, these buffer components are dissolved from the filter and enter the filtered sample, thereby enabling the assay, as these specific salts, proteins et cetera are generally essential for the biological assay. This means, the buffer components are stored in the filter by drying the buffer inside the filter, and by adding the fluid, in particular, saliva or blood, these buffer components 're-enter' and contribute to the assay, i.e. they redisperse.

Alternatively, the fluid sample can be mixed with a buffer fluid, wherein subsequently the buffered sample can be applied to the fluid providing apparatus 34, in particular, to the cartridge. In this case, preferentially, the filter does not comprise buffer components.

The filter is preferentially adapted to filter solid parts and/or specific proteins out, depending on how the filter is 'functionalized', i.e. how the filter is adapted to retain certain substances, in particular, molecules like proteins. The filter is preferentially adapted such that substances are filtered out, which disturb the analysis, in particular, the measurement, in the analyzing section.

The fluid providing apparatus 34 further comprises an analyzing section 11 for analyzing the fluid, which has been released from the fluid transferring element 1 and which has, in this embodiment, been filtered, by interacting with an analyzing unit of a fluid analyzing apparatus, which will be described further below.

Figure 2:
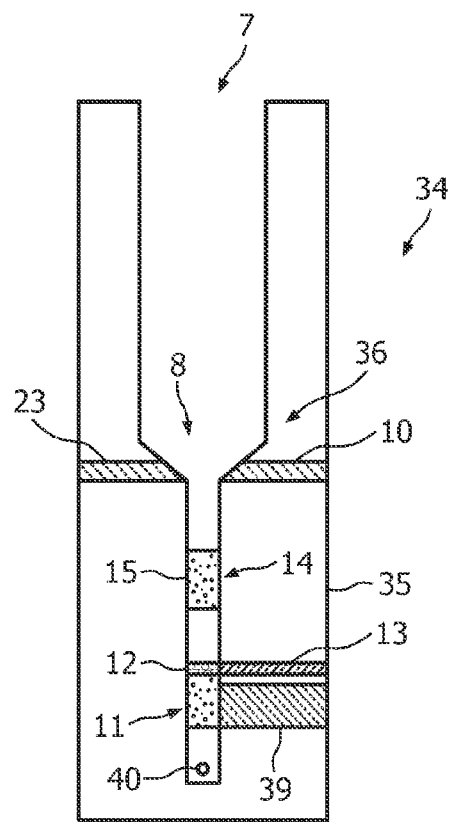
FIG. 2 shows schematically and exemplarily a sectional view of an embodiment of a fluid providing apparatus.

The casing 35 further comprises a fluid detection section 12 for detecting whether the fluid has entered the analyzing section 11 by interacting with a fluid detection unit of the analyzing apparatus 33, which will be described further below. In this embodiment, the fluid detection section 12 is a part of the analyzing section 11 and is located at the beginning of the analyzing section 11 with respect to the flow direction of the fluid. The fluid detection section 12 comprises an optical transparent portion 13 for allowing to optically detect whether the fluid has entered the analyzing section 11. The shape of the optical transparent portion 13 is shown in FIG. 2 only schematically. The shape of the optically transparent portion 13 is adapted such that it allows light of the fluid detection unit of the analyzing apparatus 33 to enter and leave the casing 35, in particular, the optically transparent portion, as required by the fluid detection unit.

Also the analyzing section 11 preferentially comprises an optically transparent portion 39, which allows to optically analyze the fluid within the analyzing section 11. The optically transparent portion 13 and the optically transparent portion 39 can be a single optically transparent portion or they can be two or more optically transparent portions.

The casing 35 further comprises a vent 40, which allows the fluid or other gas or liquid to leave the analyzing section 11, in particular, the part of the casing following the analyzing section 11.

Figure 3:
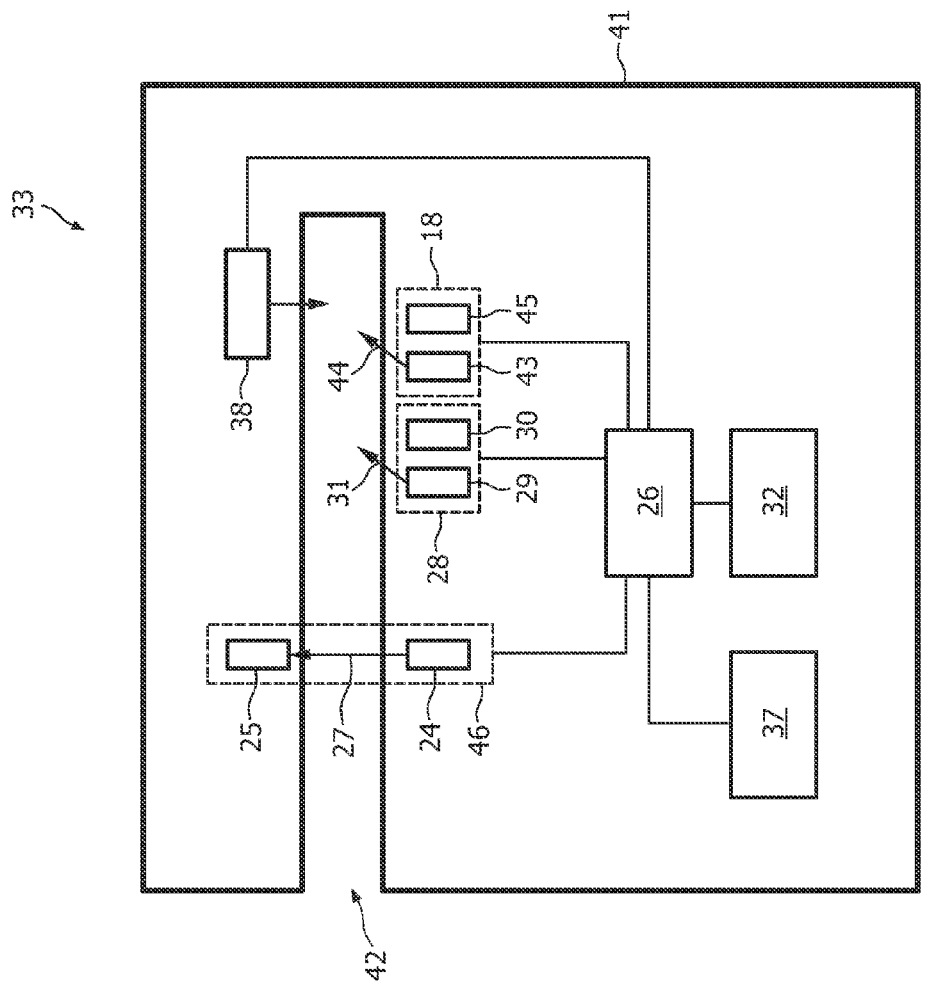
FIG. 3 shows schematically and exemplarily an embodiment of an analyzing apparatus.

FIG. 3 shows schematically and exemplarily an embodiment of an analyzing apparatus 33 for analyzing a fluid provided by the fluid providing apparatus 34, wherein the analyzing apparatus 33 comprises an opening 42, in particular, a cavity 42, into which the fluid providing apparatus 34 is introducible. The analyzing apparatus 33 comprises a fluid transferring element detection unit 46 for detecting whether the fluid transferring element 1, in particular, in this embodiment, the swab-stick 1, is introduced into the casing 35, which has been introduced into the opening 42 of the analyzing apparatus 33, by interacting with the fluid transferring element detection section 36 of the fluid providing apparatus 34.

The fluid transferring element detection unit 34 comprises a light source 24 for generating fluid transferring element detection light 27 for entering the fluid transferring element detection section 36 of the fluid providing apparatus 34 through the at least one optically transparent portion 10, 23 of the fluid transferring element detection section 36 of the fluid providing apparatus 34. The fluid transferring element detection unit 46 further comprises a transmitted light detector 25 for detecting transmitted light transmitted through the fluid transferring element detection section 36 through the at least one optical transparent portion 10, 23 for optically detecting whether the fluid transferring element 1 has been introduced into the casing 35 of the fluid providing apparatus 34. If the fluid providing apparatus 34 has been introduced into the opening 42 of the analyzing apparatus 33 and if the fluid transferring element 1 has not been introduced into the casing 35 of the fluid providing apparatus 34, the fluid transferring element detection light 27 can transmit through the transferring element detection section 36 of the fluid providing apparatus 34 and can be detected by the transmitted light detector 25, i.e. it can be detected that the fluid transferring element has not been introduced into the fluid providing apparatus 34. If the fluid transferring element 1 has been introduced into the fluid transferring element detection section 36 of the fluid providing apparatus 34, the fluid transferring element 1 blocks at least partly the fluid transferring element detection light 27 and the intensity of this light decreases, in particular, this light cannot be detected by the transmitted light detector 25 anymore, thereby detecting that the fluid transferring element 1 has been introduced into the casing 35 of the fluid providing apparatus 34, in particular, into the fluid transferring element detection section 36 of the fluid providing apparatus 34.

The analyzing apparatus 33 further comprises an analyzing unit 18 for analyzing fluid released from the fluid transferring element 1 by a fluid releasing section 8 of the fluid providing apparatus 34 by interacting with the analyzing section 11 of the fluid providing apparatus 34, wherein the analyzing unit 18 comprises an analyzing mode and a non-analyzing mode. The analyzing unit 18 comprises an analyzing light source 43 emitting analyzing light 44 for analyzing the fluid present in the analyzing section 11 of the fluid providing apparatus 34 and an analyzing detector 45 for detecting the analyzing light 44.

The analyzing unit 18 and the corresponding analyzing section 11 with the optically transparent opening 39 are preferentially adapted such that the fluid can be analyzed by using frustrated total internal reflection. An embodiment of such an analyzing unit and a corresponding analyzing section of a fluid providing apparatus is schematically and exemplarily shown in FIG. 4 in a sectional view.

Figure 4:
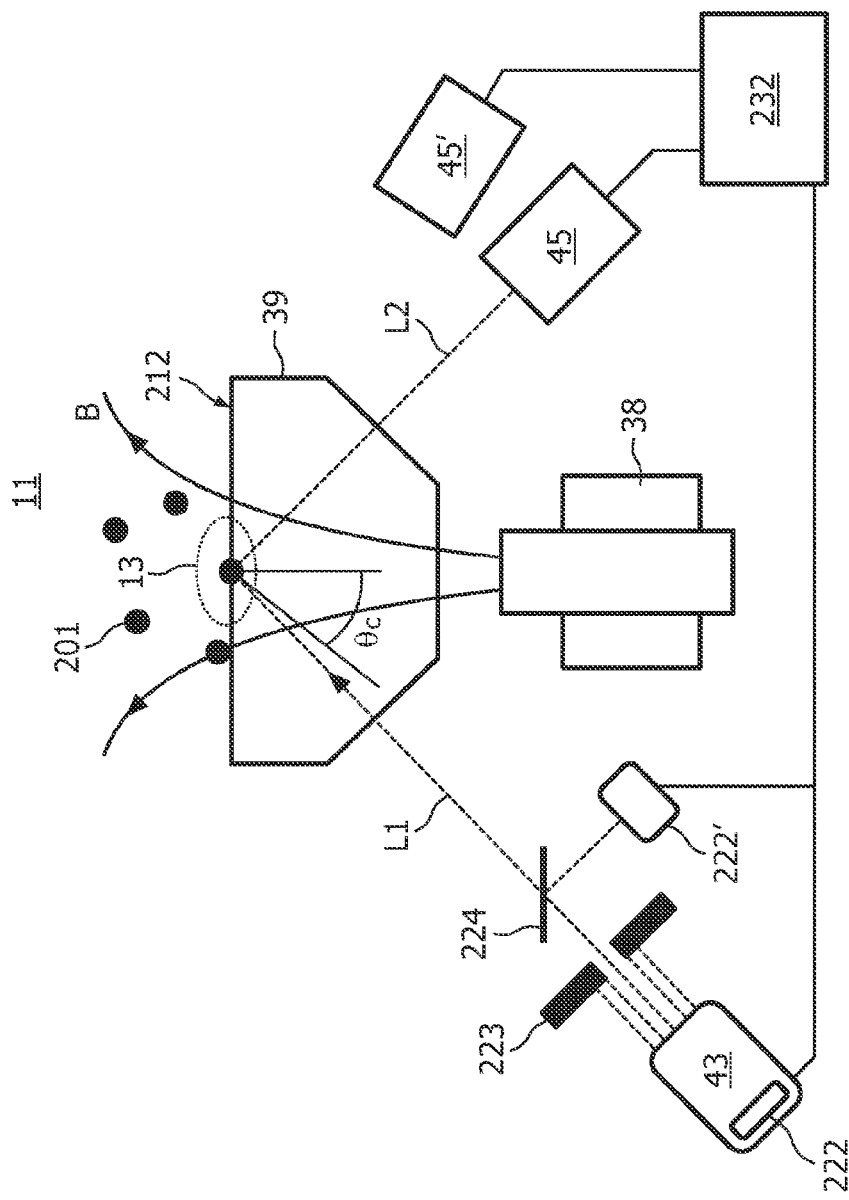
FIG. 4 shows schematically and exemplarily a principle of a reader device for analyzing a fluid in an analyzing section and an analyzing unit.

FIG. 4 shows schematically and exemplarily elements of the analyzing section 11 and of the analyzing unit 18 for analyzing the fluid by detecting particles 201, which will be explained further below. Shown is a schematic view of a reader device adapted for optical detection of a fluid to be analyzed.

The optically transparent portion 39 of the analyzing section 11 can be regarded as a carrier 39 that may for example be made from glass or transparent plastic like poly-styrene. The fluid being present in the analyzing section comprises target components to be detected (e.g. drugs, antibodies, DNA, etc.) and magnetic particles 201, for example superparamagnetic beads, wherein these particles 201 are usually bound as labels to the aforementioned target components (for simplicity only the magnetic particles 201 are shown in FIG. 4).

The interface between the carrier 39 and the analyzing section 11, which is preferentially formed as a sample chamber, is formed by a surface called "binding surface" 212. This binding surface 212 may optionally be coated with capture elements, e.g. antibodies, which can specifically bind the target components.

The sensor device comprises a magnetic unit, in particular, a magnetic field generator 38, for example an electromagnet with a coil and a core, for controllably generating a magnetic field B at the binding surface 212 and in the adjacent space of the analyzing section 11. With the help of this magnetic field B, the magnetic particles 201 can be manipulated, i.e. be magnetized and particularly be moved (if magnetic fields with gradients are used). Thus it is for example possible to attract magnetic particles 201 to the binding surface 212 in order to accelerate the binding of the associated target component to said surface.

The sensor device further comprises the light source 43, for example a laser or an LED, that generates an input light beam L1 which is transmitted into the carrier 39. The input light beam L1 arrives at the binding surface 212 at an angle larger than the critical angle $\theta_c$ of total internal reflection (TIR) and is therefore totally internally reflected as an "output light beam" L2. The output light beam L2 leaves the carrier 39 through another surface and is detected by the light detector 45, e.g. a photodiode. The light detector 45 determines the amount of light of the output light beam L2 (e.g. expressed by the light intensity of this light beam in the whole spectrum or a certain part of the spectrum). The measurement results are evaluated and optionally monitored over an observation period by an evaluation and recording module 232 that is coupled to the detector 45.

In the light source 43, a commercial DVD ($\lambda$=658 nm) laser-diode can be used. A collimator lens may be used to make the input light beam L1 parallel, and a pinhole 223 of e.g. 0.5 mm may be used to reduce the beam diameter. For accurate measurements, a highly stable light source is required. However, even with a perfectly stable power source, temperature changes in the laser can cause drifting and random changes in the output.

To address this issue, the light source may optionally have an integrated input light monitoring diode 222 for measuring the output level of the laser. The (low-pass filtered) output of the monitoring sensor 222 can then be coupled to the evaluation module 232, which can divide the (low-pass filtered) optical signal from the detector 45 by the output of the monitoring sensor 222. For an improved signal-to-noise ratio, the resulting signal may be time-averaged. The division eliminates the effect of laser output fluctuations due to power variations (no stabilized power source needed) as well as temperature drift (no precautions like Peltier elements needed).

A further improvement can be achieved if not (or not only) the laser output itself is measured, but the final output of the light source 43. As FIG. 4 coarsely illustrates, only a fraction of the laser output exits the pinhole 223. Only this fraction will be used for the actual measurement in the carrier 39, and is therefore the most direct source signal. Obviously, this fraction is related to the output of the laser, as determined by e.g. the integrated monitor diode 222, but will be affected by any mechanical change or instability in the light path (a laser beam profile is approximately elliptical with a Gaussian profile, i.e. quite non-uniform). Thus, it is advantageous to measure the amount of light of the input light beam L1 after the pinhole 223 and/or after eventual other optical components of the light source 43. This can be done in a number of ways, for example:

a parallel glass plate 224 can be placed under 45° or a beam splitter cube (e.g. 90% transmission, 10% reflection) can be inserted into the light path behind the pinhole 223 to deflect a small fraction of the light beam towards a separate input-light monitoring sensor 222;

a small mirror at the edge of the pinhole 223 or the input light beam L1 can be used to deflect a small part of the beam towards a detector.

FIG. 4 shows a "second light detector" 45' that can alternatively or additionally be used to detect fluorescence light emitted by fluorescent particles 201 which were stimulated by the evanescent wave of the input light beam L1. As this fluorescence light is usually emitted isotropically to all sides, the second detector 45' can in principle be disposed anywhere, e.g. also above the binding surface 212. Moreover, it is of course possible to use the detector 45, too, for the sampling of fluorescence light, wherein the latter may for example spectrally be discriminated from reflected light L2.

The described analyzing unit and analyzing section apply optical means for the detection of magnetic particles 201 and the target components for which detection is actually of interest. For eliminating or at least minimizing the influence of background (e.g. of the sample fluid, such as saliva, blood, etc.), the detection technique should be surface-specific. This is achieved by using the principle of frustrated total internal reflection which is explained in the following.

According to Snell's law of refraction, the angles $\theta_A$ and $\theta_B$ with respect to the normal of an interface between two media A and B satisfy the equation $$n_A \sin \theta_A = n_B \sin \theta_B$$

with $n_A$, $n_B$ being the refractive indices in medium A and B, respectively. A ray of light in a medium A with high refractive index (e.g. glass with $n_A$=2) will for example refract away from the normal under an angle $\theta_B$ at the interface with a medium B with lower refractive index such as air ($n_B$=1) or water ($n_B \approx$1.3). A part of the incident light will be reflected at the interface, with the same angle as the angle $\theta_A$ of incidence. When the angle $\theta_A$ of incidence is gradually increased, the angle $\theta_B$ of refraction will increase until it reaches 90°. The corresponding angle of incidence is called the critical angle, $\theta_c$, and is given by $\sin\theta_c = n_B/n_A$. At larger angles of incidence, all light will be reflected inside medium A (glass), hence the name "total internal reflection". However, very close to the interface between medium A (glass) and medium B (air or water), an evanescent wave is formed in medium B, which decays exponentially away from the surface. The field amplitude as function of the distance z from the surface can be expressed as:

$$\exp(-k\sqrt{n_A^2\sin^2(\theta_A)-n_B^2}\cdot z)$$

with $k=2\pi/\lambda$, $\theta_A$ being the incident angle of the totally reflected beam, and $n_A$ and $n_B$ the refractive indices of the respective associated media.

For a typical value of the wavelength $\lambda$, e.g. $\lambda=650$ nm, and $n_A=1.53$ and $n_B=1.33$, the field amplitude has declined to $\exp(-1)\approx0.37$ of its original value after a distance z of about 228 nm. When this evanescent wave interacts with another medium like the magnetic particles 201 in the setup of FIG. 4, part of the incident light will be coupled into the sample fluid (this is called "frustrated total internal reflection"), and the reflected intensity will be reduced (while the reflected intensity will be 100% for a clean interface and no interaction). Depending on the amount of disturbance, i.e. the amount of magnetic beads on or very near (within about 200 nm) to the binding surface 212 (not in the rest of the analyzing section 11, in particular, the sample chamber 11), the reflected intensity will drop accordingly. This intensity drop is a direct measure for the amount of bonded magnetic beads 201, and therefore for the concentration of target molecules. When the mentioned interaction distance of the evanescent wave of about 200 nm is compared with the typical dimensions of antibodies, target molecules and magnetic beads, it is clear that the influence of the background will be minimal. Larger wavelengths $\lambda$ will increase the interaction distance, but the influence of the background liquid will still be very small.

The described procedure is independent of applied magnetic fields. This allows real-time optical monitoring of preparation, measurement and washing steps. The monitored signals can also be used to control the measurement or the individual process steps.

For the materials of a typical application, medium A of the carrier 39 can be glass and/or some transparent plastic with a typical refractive index of 1.52. Medium B in the analyzing section 11, in particular, in the sample chamber 11, will be water-based and have a refractive index close to 1.3. This corresponds to a critical angle $\theta_c$ of 60°. An angle of incidence of 70° is therefore a practical choice to allow fluid media with a somewhat larger refractive index (assuming $n_A=1.52$, $n_B$ is allowed up to a maximum of 1.43). Higher values of $n_B$ would require a larger $n_A$ and/or larger angles of incidence.

The fluid is preferentially analyzed by using a so-called sandwich assay. The particles, which are preferentially magnetic beads, are coated with a specific antibody that attaches to a target molecule present in a fluid like blood or saliva. When the magnetic beads, that are freely present in the fluid after having been dispersed in the fluid, have reacted with the available target molecules, the beads are attracted to the detection surface that has been coated with another antibody that can couple to the target molecule. The attraction force for attracting the magnetic beads with the attached target molecules to the detection surface is a magnetic force generated by the magnetic field generator 38. After a sufficiently long reaction time the magnetic field is switched such that the magnetic beads, which are not bound to the detection surface, are pulled away from the detection surface, so that only the specifically bound magnetic beads with the target molecules, which are bound to the corresponding antibodies, remain attached to the detection surface. The magnetic beads on the detection surface can be detected optically by the above described FTIR technique. Thus, by detecting the particles 201 on the detection surface 212, the concentration of the target molecule in the fluid can be determined.

In an embodiment, the analyzing unit and the analyzing section form a biosensor based on the optical detection of super-paramagnetic labels on the detection surface, which can also be called beads and which are preferentially the particles. Instead of optical detection the magnetic particles can also be detected magnetically.

The analyzing unit and the analyzing section are preferentially adapted to detect specific target molecules, like drugs or cardiac markers, in a fluid, like saliva or blood, by determining the amount of particles, in particular, magnetic particles, bound at binding sites on the detection surface. The binding elements are preferentially antibodies and/or drug molecules, which specifically bind to the target molecules, to which an attaching element with a magnetic particle has been attached.

In particular, the particles are magnetic beads and the attaching elements are primary antibodies on the magnetic beads, and at the binding sides secondary antibodies are present. The primary and secondary antibodies bind to different parts of the analyte (target element), i.e. the primary and secondary antibodies are preferentially primary and secondary anti-PTH/anti-troponin antibodies, respectively.

If in other embodiments an inhibition assay is used instead or in addition to a sandwich assay, the particles comprising attaching elements are, for example, opiate magnetic particles, amphetamine magnetic particles, cocaine magnetic particles or methamphetamine magnetic particles and the corresponding binding sites are, for example, opiate conjugated with bovine serum albumin, amphetamine conjugated with bovine serum albumin, cocaine conjugated with bovine serum albumin and methamphetamine conjugated with bovine serum albumin.

The analyzing apparatus 33 further comprises a control unit 26 for controlling the fluid transferring element detection unit 46 and the analyzing unit 18 such that the analyzing unit 18 is switched from the non-analyzing mode to the analyzing mode, if the fluid transferring element detection unit 46 determines that the fluid transferring element 1 has been introduced into the casing 35 of the fluid providing apparatus 34, in particular, has been introduced into the fluid transferring element detection section 36 of the fluid providing apparatus 34.

The analyzing apparatus 33 further comprises a fluid detection unit 28 for detecting whether the fluid has entered the analyzing section 11 of the fluid providing apparatus 34 by interacting with the fluid detection section 12 of the fluid providing apparatus 34, in particular, by interacting with the at least one optically transparent portion 13 of the fluid detection section 12 of the fluid providing apparatus 34. The fluid detection unit 28 comprises a light source 29 for generating fluid detection light 31 and a fluid detection light detector 30 for optically detecting whether the fluid has entered the analyzing section 11 of the fluid providing apparatus 34.

In order to achieve reliable and precise results with the analyzing apparatus 33, the analyzing section should be properly filled with the fluid. This is particularly true if no active transport means are available so that the transport of fluid throughout the fluid providing apparatus 34 is entirely dependent on capillary filling. It is therefore desirable to have a fluid detection section and a corresponding fluid detection unit, which can be regarded as a wetting detector, for detecting if the analyzing section is filled properly and/or entirely. Preferably, such a wetting detection should be contactless so that no wiring in/to/from the fluid providing apparatus 34 is needed, adding to robustness and leading to cost reduction.

To address the above issues, a technique for detecting the presence of a fluid in the analyzing section of the fluid providing apparatus 34 is proposed and explained in the following with respect to FIGS. 5 and 6. In an embodiment, this technique may use the main reflection branch in the optical setup of the analyzing apparatus 33 for wetting detection. Consequently the same optics as being used for probing the bioassay can be used for wetting detection (e.g. optics that measures FTIR at a smooth contact surface, or optics measuring an output light beam at the optical structures described above).

A central idea of such a technique is to use the difference in critical angle at which TIR occurs, for the polystyrene-water (in case of wetting) and polystyrene-air (no wetting) interfaces. The refractive optical structure 350 can thus be made such that in the case of no wetting TIR at the refracting interface occurs, whereas in the case of wetting no TIR occurs. In the latter case the light is being transmitted via the polystyrene-water interface and is (partially) captured by the optical structure and redirected ("reflected back") into the fluid providing apparatus 34, in particular, into the cartridge. By carefully tuning the geometry of the optical structure, a kind of "mirroring" retro-"reflector" (however, using refraction instead of reflection) can be made where the light is two times refracted at the carrier-liquid and liquid-carrier interfaces. The design can also be used in a more quantitative manner where the measured signal is a direct measure for the refractive index of the fluid on top of the carrier. The wedge-like optical structure 350 can for example be embossed in a plastic carrier substrate.

Figure 5:
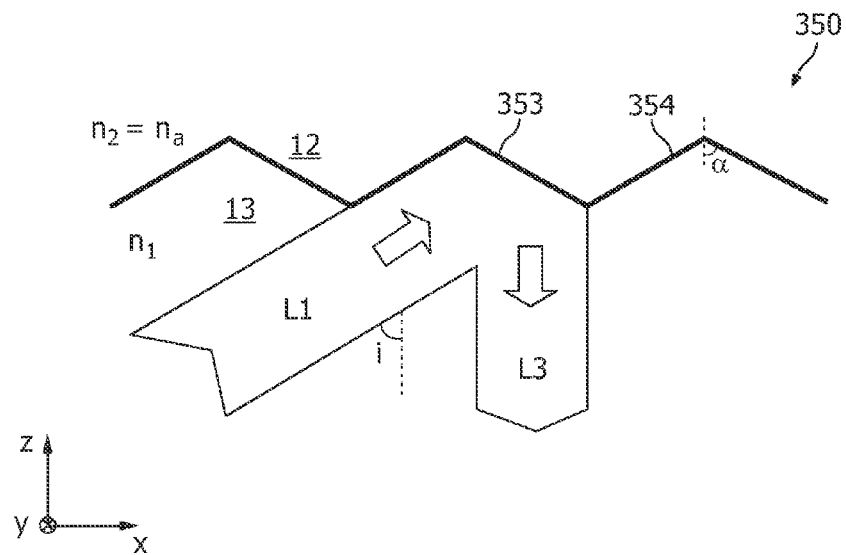
FIGS. 5 and 6 show schematically and exemplarily a principle of detecting a fluid in the analyzing section.

FIG. 5 shows a situation in which the fluid detection section 11 is filled with air having a refractive index $n_a=1$. FIG. 6 shows a situation in which the fluid detection section is filled with a water-like liquid having a refractive index $n_w$.

The critical angle $\theta_c$ for TIR at an optical interface going from high refractive index $n_1$ to low refractive index $n_2$ is given by the relation $\sin(\theta_c)=n_2/n_1$. In case of the optically transparent portion 13 of the fluid detection section 12 being a polystyrene carrier 13 with refractive index $n_1=1.58$ and a water-like fluid with refractive index $n_2=n_w=1.33$, the critical angle is $\theta_{cw}=57.3°$ when the fluid detection section 12 is filled with the fluid. If the fluid detection section 12 is however filled with air, the critical angle becomes $\theta_{ca}=39.3°$.

In FIG. 5, the angle of incidence of the input light beam L1 (with respect to the excitation facet 353) is larger than the critical angle $\theta_{ca}$ for air in the fluid detection section 12. Therefore, the input light beam L1 is totally internally reflected at the excitation facet 353 of the optical structure 350 into a TIR light beam L3 propagating under quite a different angle with respect to the surface normal than the input light beam L1.

Figure 6:
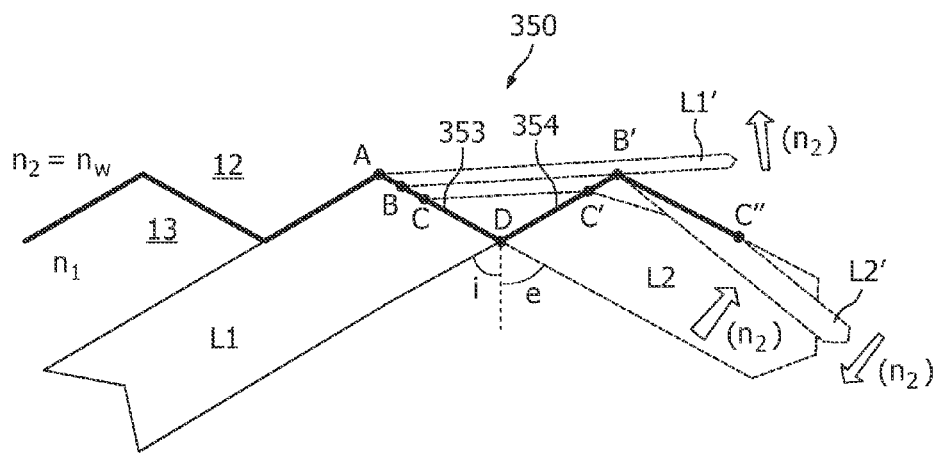

In FIG. 6, the fluid detection section 12 is filled with a water-like liquid of refractive index $n_w$. The critical angle of TIR is now such that no total internal reflection occurs at the excitation facet 353, but a normal refraction of the input light beam L1 into the fluid detection section 12. In the illustrated situation, three different cases can then be distinguished:

1. Input light leaving the excitation facet 353 between points A and B travels past the next wedge and into the sample as a light beam L1'. As indicated by the arrow with index "($n_2$)", the inclination of this light beam L1' (with respect to the horizontal) become steeper and the amount of light in it becomes higher if the refractive index $n_2$ increases.
2. Input light leaving the excitation facet 353 between points B and C is collected between points B' and C' of the collection facet 354 of the neighboring wedge; it is then totally internally reflected between points B' and C" of the excitation facet of this wedge, and leaves the carrier 13 as a secondary component L2' of the total output light. The inclination of this secondary component L2' becomes steeper and its amount of light higher if the refractive index $n_2$ increases.
3. Input light leaving the excitation facet 353 between points C and D is collected between points C' and D of the collection facet 354 of the neighboring wedge; it then propagates without further interference with the optical structure 350 through the carrier 13 as a primary component L2 of the total output light. The inclination of this primary component L2 becomes less steep (more horizontal) and its amount of light lower with increasing refractive index $n_2$.

FIGS. 5 and 6 show that only part of the light will be refracted back into the carrier 13 in the case of wetting, resulting in a back-"reflection" efficiency of clearly less than 100%. It should be noted that both the primary output light beam L2 and/or the secondary output light beam L2' can be used as wetting signal.

In a typical realization of the aforementioned analyzing apparatus 33 using FTIR, the entrance angle of the input light beam with respect to the normal of the contact surface is fixed at 70°, i.e. sufficiently larger than the critical angle both for a filled and empty analyzing section. The FTIR principle comprises monitoring a decrease of intensity of the main TIR-reflected beam, due to scattering and/or absorption of light at bound target particles; consequently, the angle of the detection branch is also making an angle of 70° with respect to the surface normal. Given this geometry, total internal reflection occurs irrespectively of wetting conditions.

However, by providing the carrier (preferably next to, near or integrated into the analyzing section) with an optical structure 350 like that of FIGS. 5 and 6, one can obtain a situation where light is being "reflected" towards the main light detector (e.g. CCD sensor) only in the case of wetting conditions (cf. beams L2, L2' in FIG. 6). Under the conditions of no wetting, total internal reflection occurs (cf. beam L3 in FIG. 5) in a direction substantially different from the main FTIR beam, and no light is being reflected towards the main light detector.

For example in case both the wedge angle α and the angle i between input light beam L1 and contact surface normal equal 70°, the input light beam L1 makes an angle of 50° with respect to the excitation facet 353. This is somewhere in the middle of the two critical angles $\theta_{ca}=39.3°$ and $\theta_{cw}=57.3°$. When no wetting occurs (FIG. 5), the incoming beam L1 is therefore totally internal reflected as light beam L3 in a direction such that the FTIR light detector does not see any light (due to the limited collection NA of the detection optics), resulting in a zero (dark) signal. When wetting occurs, the input light beam L1 is transmitted into the fluid and part of the rays being transmitted are again refracted at the rising edge of the refractive optical structure (FIG. 6).

For given refractive indices $n_1$ and $n_2$, the geometry can be chosen such that the entrance angle i of the input light beam L1 exactly equals the exit angle e of the primary component L2 of the output light beam, thereby mimicking the operation principle of a retro-reflector and giving a signal increase (bright) of the FTIR light detector. For a typical configuration with a polystyrene carrier and a water interface this results in a wedge angle α of 74 degrees.

A carrier with an optical structure 350 of the kind described above can for example be manufactured with the help of an aluminum or a NiP insert used in an injection molding process to produce polystyrene cartridges. The necessary structures may be formed in the inserts by a diamond milling process or by 3d focused ion beam (FIB) milling.

Figure 7:
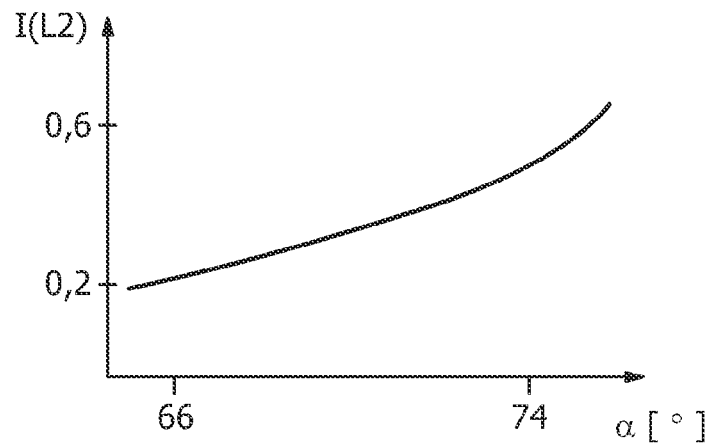
FIGS. 7 to 11 illustrate the dependency of various parameters on a wedge angle of wedges of an optically transparent portion within a fluid detection section of the fluid providing apparatus and on the refractive index of this optically transparent portion, respectively.
Figure 8:
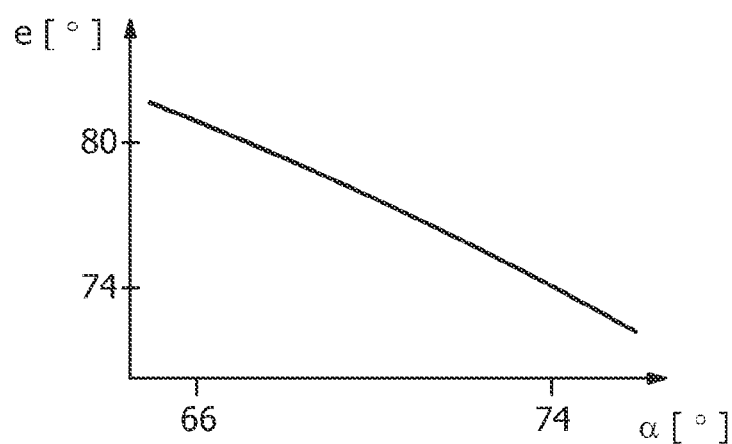

The amount of light in the primary output light beam L2 that is refracted towards a detector under any chosen direction can be optimized by a proper design of the wedge structure 350. The graph in FIG. 7 shows the outcome of a simulation for a wetting structure with polystyrene against water and an entrance angle of i=70°, where the wedge angle α is varied from 65° to 75° (vertical axis: normalized main reflected intensity I(L2)). FIG. 8 shows the corresponding exit angle e of the primary output light beam L2.

Figure 9:
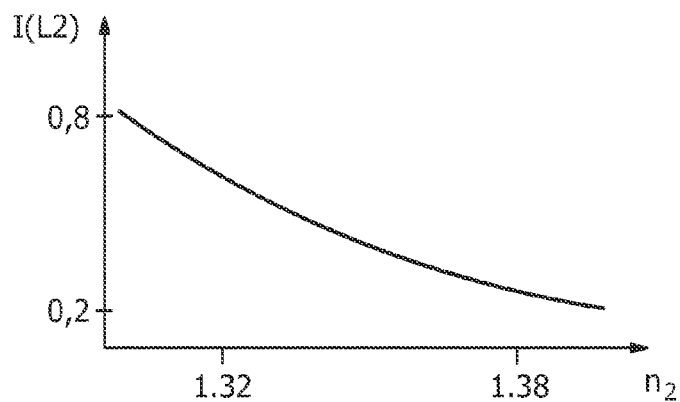
Figure 10:
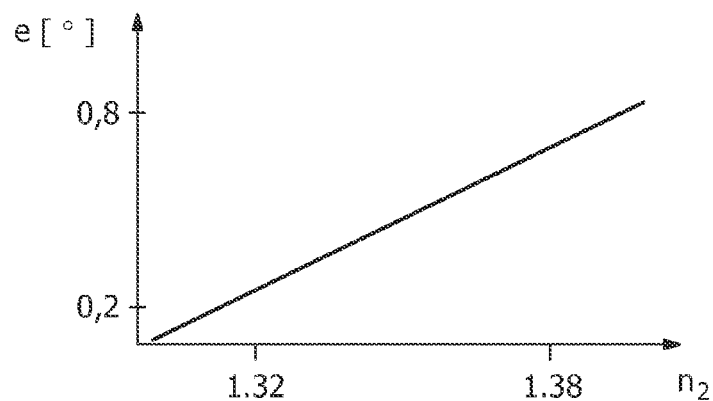
Figure 11:
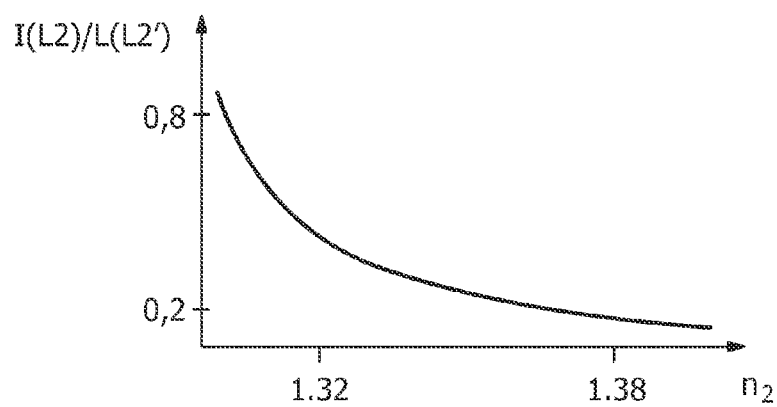

Since the described wetting sensor uses entrance angles close to the critical angle, the refraction angles are very sensitive to changes in refractive index. Consequently the sensor can also be used as a refractive index sensor. FIGS. 9 to 11 show the results of a simulation where the refractive index $n_2$ of the water-like liquid has been varied from 1.3 to 1.4. Several quantities can be used in order to extract the refractive index $n_2$ from the measured signals, for example:

The intensity I (L2) of the primary output light beam L2 (FIG. 9, normalized units on vertical axis).

The angle e of "reflection" of the primary output light beam L2 using e.g. a position sensitive diode (FIG. 9).

The ratio I (L2)/I(L2') of intensities of the primary output light beam L2 and the secondary output light beam L2' (FIG. 11).

In another embodiment the optical structure 350 may be comprised of a regular array of slanted/tilted structures where the slanting angle of the structures (and therefore also the pitch of the grooves) is linearly increased/decreased as a function of their x-position, i.e. along the surface. When the structure is now being imaged onto a 2D-detector or line array, a cutoff in light detection arises at the position where total internal reflection occurs. Given the refractive index $n_1$ of the carrier and the geometry of the optical structure 350, the position of this cutoff (in mm, or detector pixels) is a direct measure for the index of refraction $n_2$ of the medium in the sample chamber.

Figure 12:
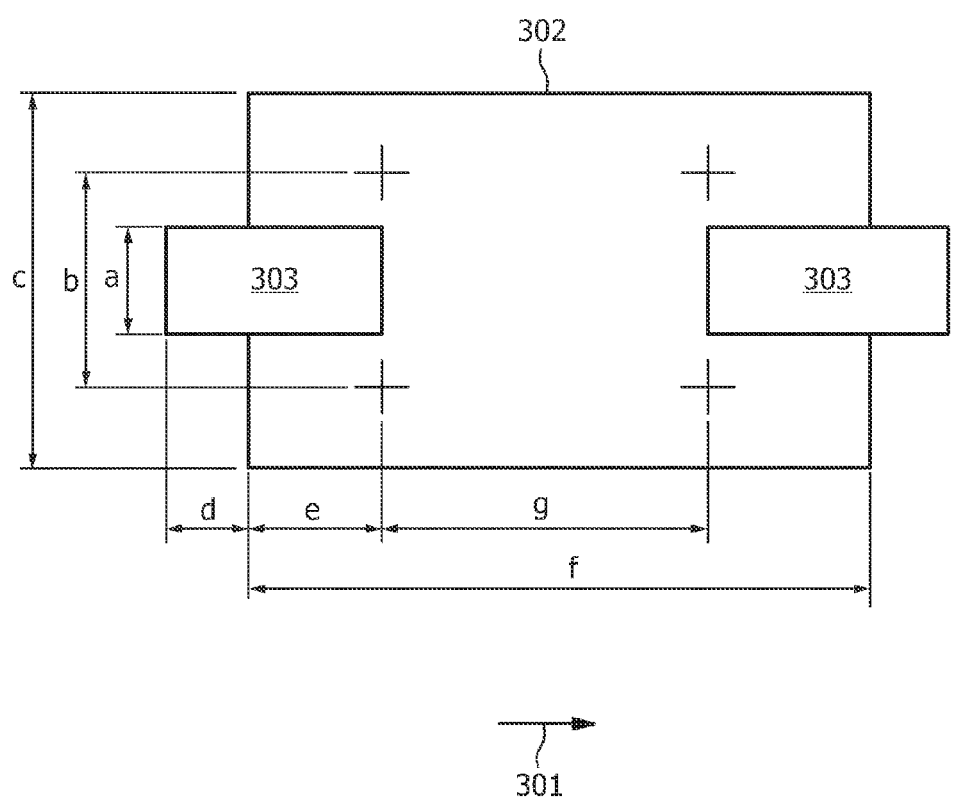
FIG. 12 shows an embodiment of an optically transparent portion of an analyzing section of a fluid providing apparatus and optically transparent portions of a fluid detection section of the fluid providing apparatus, which are partially integrated into the optically transparent portion of the analyzing section.

FIG. 12 shows schematically and exemplarily an embodiment of an optically transparent portion 302 of the analyzing section, wherein two optically transparent portions 303 of the fluid determination section are partially integrated in the optically transparent portion 302. With respect to the flow direction 301 of the fluid, a first optically transparent portion 303 is located at the beginning of the optically transparent portion 302 and a second optically transparent portion 303 is located at the end of the optically transparent portion 302. The optically transparent portions 303 are preferentially shaped as defined in FIGS. 5 and 6 and the optically transparent portion 302 is preferentially smooth, but can also comprise wedges as described above with reference to FIGS. 5 and 6. The dimensions of the lengths shown in FIG. 12 are preferentially the following: a equal to 300 μm, b equal to 900 μm, c equal to 1400 μm, d equal to 350 μm, e equal to 350 μm, f equal to 1800 μm and g equal to 1100 μm.

The analyzing apparatus 33 comprises a determination unit 32 for determining whether after a predetermined time interval after a detection of the fluid transferring element 1 by the fluid transferring element detection unit 34 the fluid has not been detected by the fluid detection unit 28. The analyzing apparatus 33 further comprises an output unit 37 for outputting a signal, if the determination unit 32 determines that after a predetermined time interval after detection of the fluid transferring element 1 by the fluid transferring element detection unit 34 the fluid has not been detected by the fluid detection unit 28. The output unit 37 is preferentially adapted to provide an acoustical and/or optical output. The output unit 37 is, for example, a display adapted for displaying an alert message.

In this embodiment, the control unit 26 is adapted to switch the analyzing unit 18 to the non-analyzing mode, if the determination unit 32 determines that after a predetermined time interval after a detection of the fluid transferring element 1 by the fluid transferring element detection unit 46 the fluid has not been detected by the fluid detection unit 28. In this case, preferentially the analyzing unit 18 is switched off. In a further embodiment, in this case the complete analyzing apparatus 33 is switched off.

The control unit 26 is preferentially adapted to control the fluid transferring element detection unit 46, the fluid detection unit 28, the analyzing unit 18, the determination unit 32 and the output unit 37.

The different units are enclosed within a casing 41, which can be shaped such that the analyzing apparatus 33 is operable as a handheld analyzing apparatus 33, which can also be denoted as a handheld reader.

The analyzing apparatus 33 further comprises a magnetic field generator 38 for generating a magnetic field within the analyzing section 11 of the fluid providing apparatus 34, which can be used to analyze the fluid as described above with reference to FIG. 4.

Figure 13:
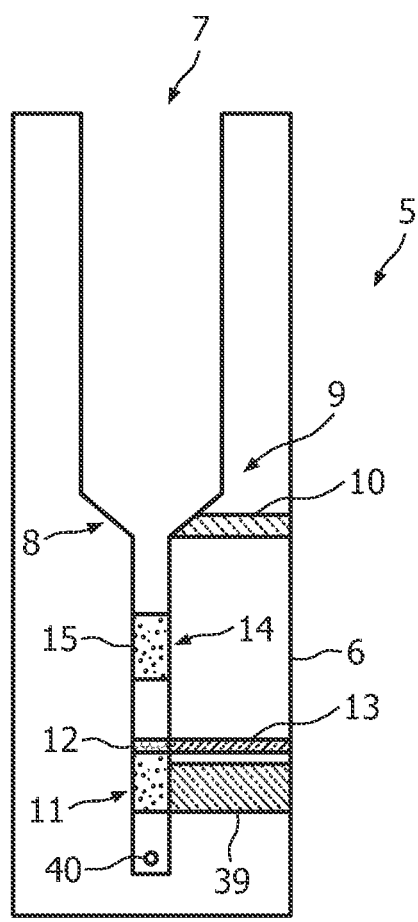
FIG. 13 shows schematically and exemplarily a sectional view of an embodiment of a fluid providing apparatus.

A further embodiment of a fluid providing apparatus 5 is schematically and exemplarily shown in a sectional view in FIG. 13.

Elements and sections of the fluid providing apparatus 5 shown in FIG. 13, which are similar or identical to the sections and elements of the fluid providing apparatus 34 shown in FIG. 2, are denoted by the same reference numbers. For a description of these sections and elements reference is made to the above explanation with respect to FIG. 2.

The fluid providing apparatus 5 comprises a fluid transferring element detection section 9 for detecting whether the fluid transferring element 1 is introduced into the casing 6 by interacting with a fluid transferring element detection unit of the fluid analyzing apparatus 33, which will be described further below. The fluid transferring element detection section 9 comprises one optical transparent portion 10 for allowing to optically detect whether the fluid transferring element 1 has been introduced into the casing 6. This optical transparent portion 10 is adapted such that light can enter the fluid transferring element detection section and such that light reflected by the fluid transferring element 1 can leave the casing 6 for being detected by a corresponding detector of the analyzing apparatus 33, which will be described further below.

Figure 14:
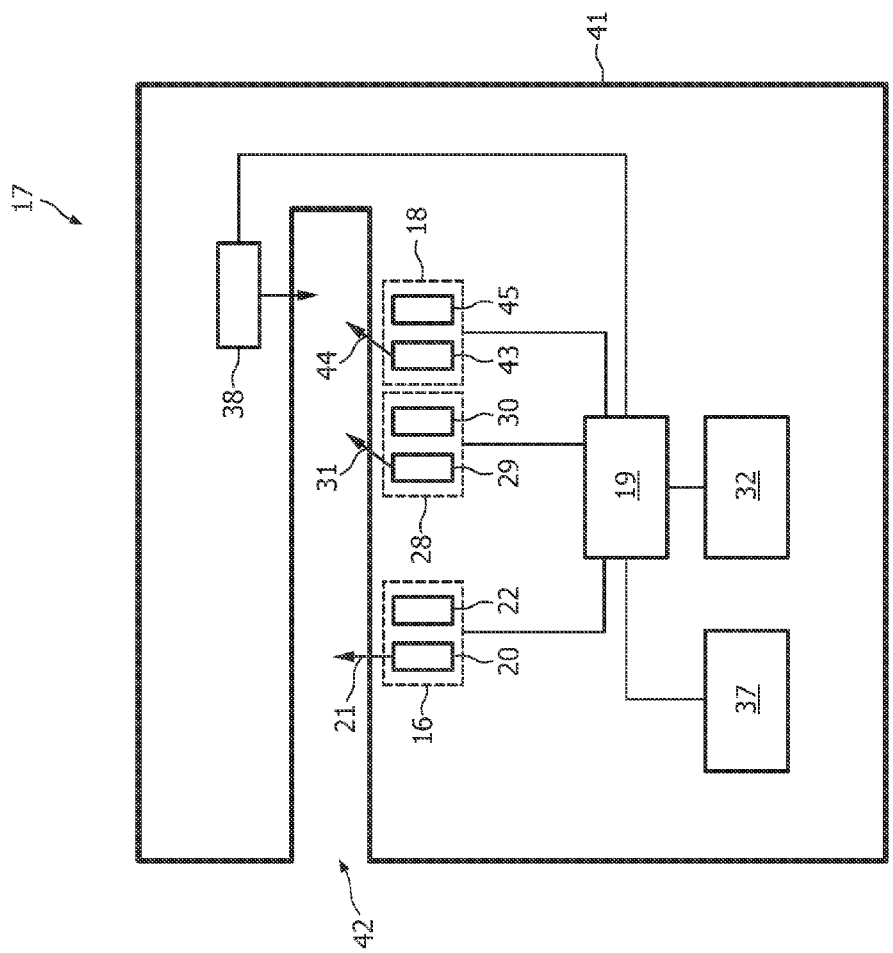
FIG. 14 shows schematically and exemplarily an embodiment of an analyzing apparatus.

FIG. 14 shows schematically and exemplarily a further embodiment of an analyzing apparatus 17, which corresponds to the fluid providing apparatus 5 shown in FIG. 13.

Elements of the analyzing apparatus 17, which are identical or similar to elements of the analyzing apparatus 17 are denoted by the same reference numbers. For a description of these elements reference is made to the above explanation with respect to FIG. 3.

The analyzing apparatus 17 comprises a fluid transferring element detection unit 16 for detecting whether the fluid transferring element 1 is introduced into the casing 6 by interacting with a fluid transferring element detection section 9 of the fluid providing apparatus 5. The fluid transferring element detection unit 16 comprises a light source 24 generating fluid transferring element detection light 21 for entering the fluid transferring element detection section 9 of the fluid providing apparatus 5 through the optical transparent portion 10 of the fluid transferring element detection section 9. The fluid transferring element detection unit 16 further comprises a reflected light detector 22 for detecting reflected light reflected by the fluid transferring element 1 for optically detecting whether the fluid transferring element 1 is introduced into the casing 6 of the fluid providing apparatus 5.

The analyzing apparatus 17 comprises a control unit 19, which corresponds to the control unit 26 of the analyzing apparatus 17, and which is at least adapted to control the fluid transferring element detection unit 16 and the analyzing unit 18 such that the analyzing unit is switched from the non-analyzing mode to the analyzing mode, if the fluid transferring element detection unit 16 determines that the fluid transferring element 1 has been introduced into the casing 6 of the fluid providing apparatus 5.

Figure 15:
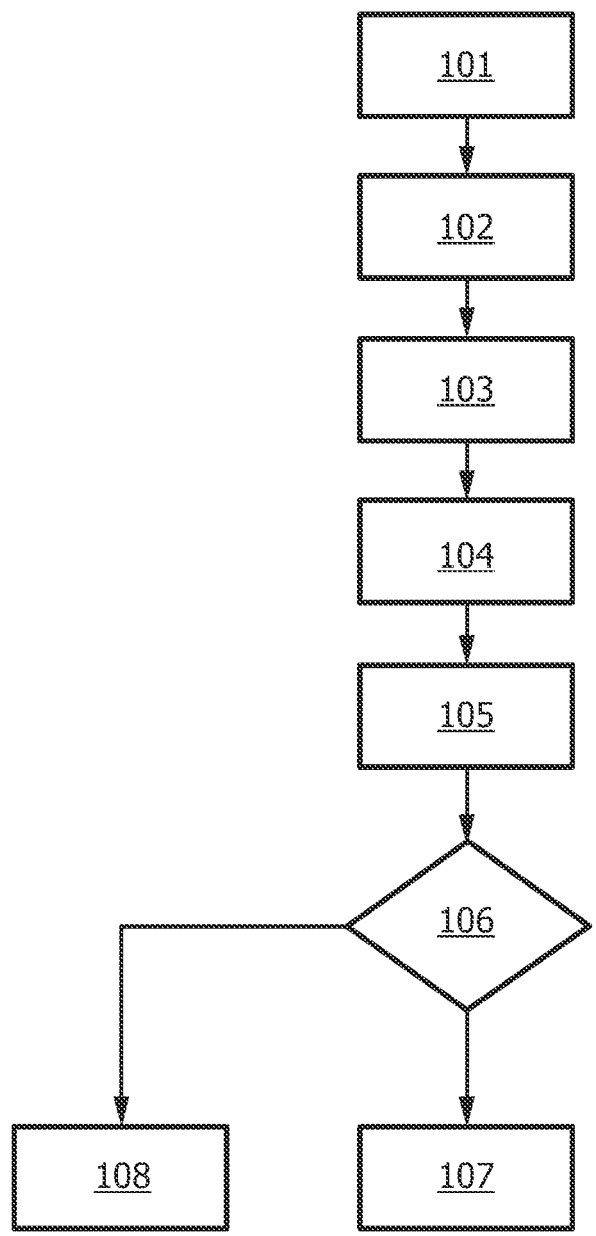
FIG. 15 shows exemplarily a flow chart illustrating an analyzing method for analyzing a fluid.

In the following an embodiment of an analyzing method for analyzing a fluid provided by a fluid providing apparatus comprising a casing for receiving a fluid transferring element will be exemplarily described with reference to a flowchart shown in FIG. 15.

In step 101, a disposable fluid transferring element and a disposable fluid providing apparatus, which are provided within a package, are unpacked by a user.

In step 102, the fluid providing apparatus is introduced into the analyzing apparatus 17, and in step 103 a sample of a fluid, which has to be analyzed, is received by the fluid transferring element. During performing steps 102 and 103 the analyzing unit of the analyzing apparatus 17 is still in the non-analyzing mode, in particular, is still switched off. Preferentially, during performing steps 102 and 103, the complete analyzing apparatus 17 is switched off.

In step 104, the fluid transferring element is introduced into the fluid providing apparatus, which has already been introduced into the analyzing apparatus 17. In step 105, the fluid is released within the fluid releasing section of the fluid providing apparatus and preferentially at the same time the fluid transferring element detection unit detects that the fluid transferring element is introduced into the casing by interacting with the fluid transferring element detection section of the fluid providing apparatus.

After it has been detected that the fluid transferring element has been introduced into the casing of the fluid providing apparatus, in step 105 the analyzing unit of the analyzing apparatus 17 is switched from the non-analyzing mode to the analyzing mode.

The released fluid flows through the filtering section to the fluid detection section of the fluid providing apparatus and in step 106 the fluid detection unit detects whether the fluid has entered the fluid detection section, and, thus, the analyzing section of the fluid providing apparatus. Furthermore, the determination unit of the analyzing apparatus 17 determines whether the fluid has been detected after a predetermined time interval after a detection of the fluid transferring element by the fluid transferring element detection unit or not. If the fluid has been detected within the fluid detection section within the predetermined time interval after the detection of the fluid transferring element, the fluid is analyzed in the analyzing section in step 107. If the fluid has not been detected within the predetermined time interval after a detection of the fluid transferring element in the fluid detection section, for example, because the fluid has not reached the analyzing unit, in step 108 an output signal is provided to the user and preferentially the analyzing unit is switched off.

The system of the fluid providing apparatus and the analyzing apparatus 17, 33 can be provided as a frustrated total internal reflection biosensor for using in a fast drugs-of-abuse (DOA) test in, for example, saliva or blood. This biosensor could, for example, be used for a through-window roadside testing, which is similar to an alcohol testing for car drivers, and in workplace testing, in particular, for safety critical industries.

Although in the above described embodiments certain fluid detection units and fluid detection sections have been described for determining whether the fluid has entered the analyzing section of the fluid providing apparatus, in other embodiments other wetting sensors can be used for determining whether the fluid has entered the analyzing apparatus 17, 33.

In a preferred embodiment, the analyzing apparatus 17, 33 is switched off between different tests, i.e. between different analyzing procedures. Preferably, this is done automatically. For example, after an analyzing procedure has been completed and the fluid providing apparatus, which is preferentially a cartridge, has been removed from the analyzing apparatus 17, 33, this removing is detected by the analyzing apparatus 17, 33 and the analyzing unit and preferentially also the other units of the analyzing apparatus 17, 33 are switched off. If another fluid providing apparatus is inserted into the analyzing apparatus 17, 33 and if the fluid transferring element is inserted into this new fluid providing apparatus, this insertion of the fluid transferring element is detected by the fluid transferring element detection unit and the analyzing apparatus 17, 33 is switched on, in particular, the analyzing unit is switched to the analyzing mode. The detection of the fluid providing apparatus, in particular, of the cartridge, within the analyzing apparatus 17, 33 is well-known. Such a detection is for example provided in the Cozart DDS System. In most cases this detection is done by a simple mechanical switch. But, in the prior art the analyzing apparatus 17, 33 is switched on an operational mode, if the cartridge is detected within the analyzing apparatus 17, 33, irrespective of a fluid transferring element has been introduced into the cartridge or not.

The control unit 19, 26 can be adapted such that the analyzing unit is switched from a non-analyzing mode to an analyzing mode, if the fluid providing apparatus including the fluid transferring element has been introduced into the analyzing apparatus 17, 33, if the fluid transferring element has been removed from the fluid providing apparatus and if the fluid transferring element has been inserted into the analyzing apparatus 17, 33 again. The control unit can 19, 26 also be adapted such that the analyzing unit is switched from a non-analyzing mode to an analyzing mode, if the fluid providing apparatus has been introduced into the analyzing apparatus 17, 33 without including the fluid transferring element and if than the fluid transferring element is introduced into the fluid providing apparatus. The analyzing apparatus 17, 33 can comprise a switch, which allows a user to choose between different sequences of operations like introducing or removing the fluid transferring element, which lead to a switching of the analyzing unit from a non-analyzing mode to an analyzing mode or to a switching of the analyzing unit from an analyzing mode to a non-analyzing mode.

The fluid providing apparatus preferentially adapted such that at least in parts of the fluid providing apparatus the fluid is driven by capillary forces.

The light sources used in the above described embodiments are, for example, light emitting diodes and the detectors are preferentially CMOS imagers. However, in other embodiments other light sources and/or detectors can be used.

The fluid releasing section is preferentially adapted such that it is fluid tight to avoid spillage and contamination of the analyzing apparatus 17, 33. This can, for example, be achieved by using only a single piece of plastic having an optically transparent portion for different sections of the optical providing unit. If, in an embodiment, the fluid providing apparatus is made of different pieces, preferentially sealing elements like a rubber O-ring are used for making at least the fluid releasing section and the fluid transferring element detection section fluid tight.

Although in the above described embodiments a certain configuration of a fluid transferring element, a fluid providing apparatus and an analyzing apparatus 17, 33 have been described, in other embodiments, the fluid transferring element, the fluid providing apparatus and the analyzing apparatus 17, 33 can comprise another configuration, as long as the fluid transferring element is adapted to transfer a fluid like saliva or blood to the fluid providing apparatus, the fluid providing apparatus comprises an introduction opening, a fluid releasing section and a fluid transferring element detection section as defined in claim 1 and the analyzing apparatus 17, 33 comprises a fluid transferring element detection unit as defined in claim 6.

Although in the above described embodiments certain techniques for analyzing the fluid, in particular, for measuring or detecting particles in the fluid, are applied, in other embodiments the analyzing section and/or the analyzing unit 17, 33 can be adapted to analyze the fluid by another technique, in particular, by another optical technique or magnetically.

The analyzing apparatus 17, 33, the fluid providing apparatus and/or the fluid transferring element can be adapted to the presence of magnetic particles on or near to a sensor surface on any detection principle, based on any property of the particles, e.g. they can detect via magnetic methods (e.g. magnetoresistive, Hall, coils), optical methods (e.g. imaging, fluorescence, chemiluminescence, absorption, scattering, evanescent field techniques, surface plasmon resonance, Raman, etc.), sonic detection (e.g. surface acoustic wave, bulk acoustic wave, cantilever, quartz crystal etc), electrical detection (e.g. conduction, impedance, amperometric, redox cycling), combinations thereof et cetera.

A detection of the magnetic properties of the particle on or near to a sensor surface can be performed by using e.g. a coil, a magneto-resistive sensor, a magneto-restrictive sensor, a Hall sensor, a planar Hall sensor, a flux gate sensor, a SQUID, a magnetic resonance sensor et cetera.

In addition to the above described molecular assays, also larger moieties can be detected, for example, cells, viruses, or fractions of cells or viruses, tissue extract, et cetera. The detection can occur with or without scanning of a sensor element with respect to the biosensor surface. Measurement data can be derived as an end-point measurement, as well as by recording signals kinetically or intermittently. Labels can be detected directly by the sensing method. As well, the particles can be further processed prior to detection. An example of further processing is that materials are added or that the (bio)chemical or physical properties of the label are modified to facilitate detection. The analyzing apparatus 17, 33, the fluid providing apparatus and/or the fluid transferring element can be used with several biochemical assay types, for example, binding/unbinding assay, sandwich assay, competition assay, displacement assay, enzymatic assay et cetera. The device, methods and systems of this invention are suited for sensor multiplexing (i.e. the parallel use of different sensors and sensor surfaces), label multiplexing (i.e. the parallel use of different types of labels) and chamber multiplexing (i.e. the parallel use of different reaction chambers). The device, methods and systems described in the present invention can be used as rapid, robust, and easy to use point-of-care biosensors for small sample volumes. Also, the device, methods and systems of the present invention can be used in automated high-throughput testing. In this case, the analyzing section of the fluid providing apparatus is e.g. a well plate or cuvette.

The above mentioned magnetic beads are preferentially nano-particles having at least one dimension ranging between 3 nm and 5000 nm, preferably between 10 nm and 3000 nm, more preferred between 50 nm and 1000 nm.

Although in the above described embodiments, different functions have been performed by several units, these functions can be performed by any other number of units or devices. For example, the analyzing section and the fluid determination section and the corresponding analyzing unit and fluid detection unit can be integrated forming a single section and a single unit, respectively, wherein, for example, the same light source and/or the same detection unit is used for fluid detection and analyzing the fluid.

Preferentially, the fluid providing apparatus and the analyzing apparatus 17, 33 comprise alignment means for aligning the fluid providing apparatus and the analyzing apparatus 17, 33 with respect to each other, in particular, for aligning the fluid transferring element detection section with respect to the fluid transferring element detection unit, the fluid detection section with respect to the fluid detection unit and the analyzing section with respect to the analyzing unit 17, 33. The alignment means are, for example, engaging means provided on the fluid providing apparatus and/or the analyzing apparatus 17, 33, which engage, if the fluid providing apparatus and the analyzing apparatus 17, 33 are aligned with respect to each other, for holding the fluid providing apparatus within the analyzing apparatus 17, 33 in the aligned position.

Other variations to the disclosed embodiments can be understood and effected by those skilled in the art in practicing the claimed invention, from a study of the drawings, the disclosure, and the appended claims.

In the claims, the word "comprising" does not exclude other elements or steps, and the indefinite article "a" or "an" does not exclude a plurality.

A single unit or a device may fulfill the functions of several items recited in the claims. The mere fact that certain measures are recited in mutually different dependent claims does not indicate that a combination of these measures cannot be used to advantage.

A computer program may be stored/distributed on a suitable medium, such as an optical storage medium or a solid-state medium, supplied together with or as part of other hardware, but may also be distributed in other forms, such as via the Internet or other wired or wireless telecommunication systems.

Any reference signs in the claims should not be construed as limiting the scope.

The invention claimed is:

1. A fluid analyzer comprising:
   a fluid transferring element for obtaining a sample of a fluid;
   a fluid providing apparatus for providing the fluid to an analyzing apparatus for analyzing the fluid, the fluid providing apparatus comprising a casing having:
   an introduction opening through which the fluid transferring element is introducible into the casing for transferring the fluid to the fluid providing apparatus;
   a fluid releasing section for releasing the fluid from the fluid transferring element;

a first detection section for at least detecting whether the fluid transferring element is introduced into the casing, comprising a first optically transparent opening;

a filtering section comprising a filter for storing buffer components for dispersing into the fluid and for de-bubbling the fluid;

a fluid detection section comprising a second optically transparent opening, and a wedge-shaped optical structure adjacent to the fluid-containing region of the fluid detection section;

an analyzing section adjacent to the fluid detection section, the analyzing section comprising a sample chamber having a binding surface, and a third optically transparent opening; and a vent; and an analyzing apparatus for analyzing the fluid, the analyzing apparatus comprising a housing defining a cavity into which the fluid providing apparatus is introducible into the housing, the analyzing apparatus comprising:

a first detector which detects whether the fluid providing apparatus is introduced into the housing and the fluid transferring element is introduced into the casing, the first detector comprising a first light source for generating a first light for entering the first optically transparent opening and a first light detector for detecting the first light reflected or transmitted by the fluid;

a fluid detection unit for detecting whether the fluid has entered the sample chamber, the fluid detection unit comprising a second light source for generating a second light for entering the second optically transparent opening and a second light detector for detecting the second light refracted by the wedge-shaped optical structure;

a control unit for switching on or off the analyzing apparatus depending on the detection of the fluid transferring element within the fluid providing apparatus;

an analyzing unit for analyzing the fluid, the analyzing unit comprising a third light source for generating a third light for entering the third optically transparent opening and a third light detector for detecting the third light reflected or transmitted by the fluid; and a sensor comprising a magnetic field generator for controllably generating a magnetic field at the binding surface and in the sample chamber, wherein the third light source for generating the third light for entering the third optically transparent opening and the third light detector are used for detecting the magnetic beads on the detection surface.

2. The apparatus of claim 1, wherein the fluid releasing section squeezes the fluid transferring element for releasing the fluid.

3. The apparatus of claim 1, wherein the analyzing apparatus comprises a determination unit for determining whether after a predetermined time interval after a detection of the fluid transferring element by the fluid transferring element detection unit the fluid has not been detected by the fluid detection unit.

4. A fluid analyzing system for analyzing a fluid comprising the fluid analyzer of claim 1.

* * * * *